(12) United States Patent
Marciani et al.

(10) Patent No.: US 11,013,427 B2
(45) Date of Patent: May 25, 2021

(54) MAGNETIC RESONANCE IMAGING METHODS FOR THE STUDY OF GASTROINTESTINAL TRANSIT

(71) Applicant: NOTTINGHAM UNIVERSITY HOSPITALS NHS TRUST, Nottingham (GB)

(72) Inventors: Luca Marciani, Nottingham (GB); Roy Harris, Nottingham (GB); Caroline Louise Hoad, Nottingham (GB); Penelope Anne Gowland, Nottingham (GB); Alan Christopher Perkins, Nottingham (GB); Mark Robert Fox, Nottingham (GB); Robin Charles Spiller, Nottingham (GB)

(73) Assignee: NOTTINGHAM UNIVERSITY HOSPITALS NHS TRUST, Nottingham (GB)

( * ) Notice: Subject to any disclaimer, the term of this patent is extended or adjusted under 35 U.S.C. 154(b) by 635 days.

(21) Appl. No.: 15/324,233

(22) PCT Filed: Jul. 3, 2015

(86) PCT No.: PCT/GB2015/051948
§ 371 (c)(1),
(2) Date: Jan. 5, 2017

(87) PCT Pub. No.: WO2016/005731
PCT Pub. Date: Jan. 14, 2016

(65) Prior Publication Data
US 2017/0156628 A1    Jun. 8, 2017

(30) Foreign Application Priority Data
Jul. 7, 2014    (GB) ..................................... 1412040

(51) Int. Cl.
A61B 5/05        (2021.01)
A61B 5/055       (2006.01)
(Continued)

(52) U.S. Cl.
CPC ................ *A61B 5/055* (2013.01); *A61B 5/42* (2013.01); *A61K 49/10* (2013.01); *A61K 49/18* (2013.01);
(Continued)

(58) Field of Classification Search
None
See application file for complete search history.

(56) References Cited

U.S. PATENT DOCUMENTS 5,538,737 A        7/1996  Thomas et al.
2007/0112339 A9*   5/2007  Ivkov ................ A61K 41/0052
                                                      606/27
(Continued)

FOREIGN PATENT DOCUMENTS

KR    20130037848 A    4/2013

OTHER PUBLICATIONS

Hoad, C., P. Rayment, V. Risse, E. Cox, E. Ciampi, S. Pregent, L. Marciani, M. Butler, R. Spiller, and P. Gowland, Encapsulation of lipid by alginate beads reduces bio-accessibility: An in vivo C-13 breath test and MRI study. Food Hydrocolloids, 2011. 25(5): p. 1190-1200.
(Continued)

*Primary Examiner* — Ankit D Tejani
(74) *Attorney, Agent, or Firm* — Troutman Pepper Hamilton Sanders LLP (Rochester)

(57) ABSTRACT

Methods and apparatus for the study of gastrointestinal transit in a human or animal subject. The method being for the study of a subject which has previously ingested a container containing first and second fluids that are detect-
(Continued)

able and distinguishable by MRI, which method comprises the steps of forming a first magnetic resonance image of at least a portion of the subject's GI tract in which the container is located, wherein the magnetizations of the first and second fluids are in-phase; forming a second magnetic resonance image, coincident with the first image, wherein the magnetizations of the first and second fluids are out-of-phase; and subtracting the second image from the first image, or vice versa, to form a composite image.

14 Claims, 1 Drawing Sheet

(51) Int. Cl.
| | |
|---|---|
| G01R 33/56 | (2006.01) |
| G01R 33/48 | (2006.01) |
| A61K 49/18 | (2006.01) |
| A61K 49/10 | (2006.01) |
| G06T 7/70 | (2017.01) |
| A61B 5/00 | (2006.01) |
| G06T 5/50 | (2006.01) |

(52) U.S. Cl.
CPC ...... *A61K 49/1806* (2013.01); *A61K 49/1818* (2013.01); *G01R 33/4828* (2013.01); *G01R 33/5601* (2013.01); *G06T 5/50* (2013.01); *G06T 7/70* (2017.01); *A61B 5/7425* (2013.01); *A61B 2576/02* (2013.01); *G06T 2207/10088* (2013.01); *G06T 2207/20221* (2013.01); *G06T 2207/20224* (2013.01); *G06T 2207/30092* (2013.01); *G06T 2207/30204* (2013.01)

(56) References Cited

U.S. PATENT DOCUMENTS

| | | | | |
|---|---|---|---|---|
| 2009/0306633 | A1* | 12/2009 | Trovato | A61B 1/041 604/891.1 |
| 2012/0114851 | A1* | 5/2012 | Kalechofsky | A61K 49/1815 427/213 |
| 2012/0301007 | A1* | 11/2012 | Shirai | A61B 5/055 382/131 |

OTHER PUBLICATIONS

Buhmann, S., C. Kirchhoff, R. Ladumer, T. Mussack, M.F. Reiser, and A. Lienemann, Assessment of colonic transit time using MRI: a feasibility study. European Radiology, 200T 17(3): p. 669-674.

Schiller, C., C.P. Frohlich, T. Giessmann, W. Siegmund, H. Monnikes, N. Hosten, and W. Weitschies, Intestinal fluid volumes and transit of dosage forms as assessed by magnetic resonance imaging. Alimentary Pharmacology and Therapeutics, 2005. 22(10): p. 971-979.

Schwarz, R., A. Kaspar, J. Seelig, and B. Kunnecke, Gastrointestinal transit times in mice and humans measured with Al-27 and F-19 nuclear magnetic resonance. Magnetic Resonance in Medicine, 2002. 48(2): p. 255-261.

Schwarz, R., M. Schuurmans, J. Seelig, and B. Kunnecke, F-19-MRI of perfluorononane as a novel contrast modality for gastrointestinal imaging. Magnetic Resonance in Medicine, 1999. 41(1): p. 80-86.

Hahn, T., S. Kozerke, W. Schwizer, M. Fried, P. Boesiger, and A. Steingoetter, Visualization and quantification of intestinal transit and motor function by real-time tracking of F-19 labeled capsules in humans. Magnetic Resonance in Medicine, 2011. 66(3): p. 812-820.

Kremser, C., K. Albrecht, M. Greindl, C. Wolf, P. Debbage, and A. Bemkop-Schnurch, In vivo determination of the time and location of mucoadhesive drug delivery systems disintegration in the gastrointestinal tract. Magnetic Resonance Imaging, 2008. 26(5): p. 638-643.

Hoad, C., P. Rayment, E. Cox, P. Wright, M. Butler, R. Spiller, and P. Gowland, Investigation of alginate beads for gastro-intestinal functionality, Part 2: In vivo characterisation. Food Hydrocolloids, 2009. 23(3): p. 833-839.

Hahn, T., S. Kozerke, W. Schwizer, M. Fried, P. Boesiger, and A. Steingoetter, F-19 MR Imaging Golden Angle-based Capsule Tracking for Intestinal Transit and Catheter Tracking: Initial in Vivo Experience. Radiology, 2012. 265(3): p. 917-925.

International Search Report and Written Opinion for corresponding Application No. PCT/GB2015/051948 (dated Dec. 14, 2015).

Placidi et al., "In vivo Gastrointestinal Transit Study Using Double-Labelled Markers," Proc. Internat. Soc. Mag. Reson. Med. 19:3497 (2011).

Chaddock et al., "Novel MRI Tests of Orocecal Transit Time and Whole Gut Transit Time: Studies in normal Subjects," Neurogatroenterol. Motility 26(2):205-214 (2014).

International Search Report and Written Opinion for corresponding Application No. PCT/GB2015/051948 (dated Jan. 10, 2017).

* cited by examiner

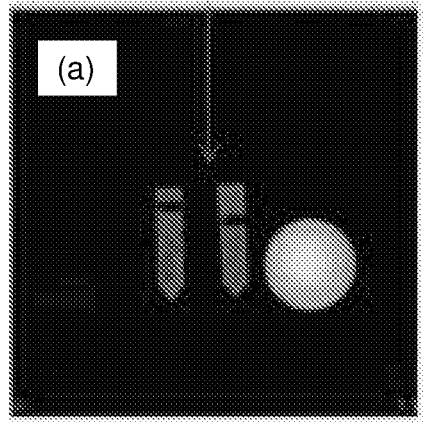
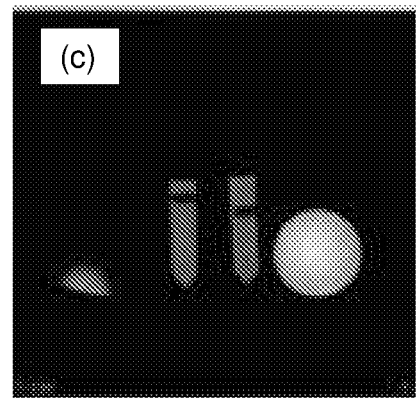
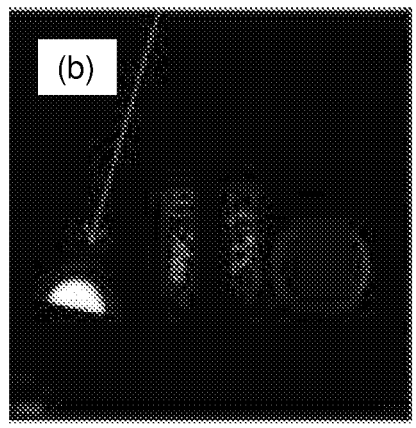
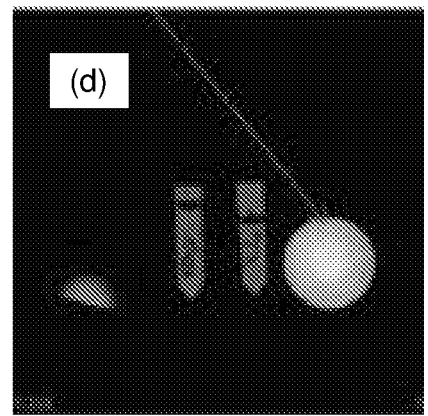
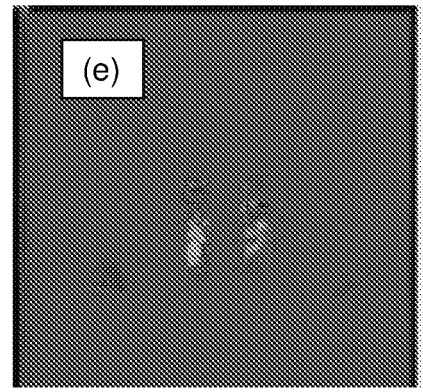

MAGNETIC RESONANCE IMAGING METHODS FOR THE STUDY OF GASTROINTESTINAL TRANSIT

This application is a national stage application under 35 U.S.C. § 371 of PCT Application No. PCT/GB2015/051948, filed Jul. 3, 2015, which claims the priority benefit of Great Britain Application No. 1412040.6, filed Jul. 7, 2014, which are hereby incorporated by reference in their entirety.

This invention relates to methods for the study of gastrointestinal transit in a human or animal subject, and to capsules and other materials useful in such methods.

Abnormalities of gastrointestinal (GI) transit (both orocoecal, small bowel and colonic transit) are a common underlying cause of gastrointestinal symptoms. The prevalence of functional GI disorders in the general population is 25-40% and this accounts for up to 40% of GI clinic consultations. Such patients often present with diffuse GI motility disorder. In particular, constipation affects 12%-19% of the population with a general estimated annual cost of US$235 m, which equates to US$7,522 per patient.

Where a subject has an abnormality of GI function it is often necessary to assess the time taken for matter (mostly food and bacterial matter) to pass through the subject's GI tract (referred to as 'GI transit time'). As well the transit time for the whole gut, small bowel transit (SBT), regional colonic transit and colonic transit may be of particular interest and relevance in the assessment of disease states. Direct assessment of GI transit time is often required to establish an accurate diagnosis and direct therapy. In some cases, the outcome of the assessment may be surgery, including stomas to flush the bowel or resection of a part of the GI tract that is not functioning properly.

Current methods of assessing GI transit are based on nuclear medicine techniques which make use of ionising radiation, such as gamma scintigraphy and X-ray. Subjects are either fed a standard meal labelled with radioactive tracers or they ingest commercially available radio-opaque markers and undergo X-ray. Such methods may be inconvenient or unpleasant for the subject, and the use of ionising radiation is generally undesirable and may be prohibited for certain groups of patients.

Other minimally invasive methods include the breath test and radio-telemetery pills. In the breath test, a $^{13}C$ tracer is ingested with a meal and its appearance later detected in the breath of the subjects. However, the $^{13}C$ label needs to be metabolised first and variability is large. Radio-telemetry pills have recently appeared on the market and received FDA approval to measure GI transit but their usefulness and reproducibility are still to be evaluated.

Magnetic resonance imaging (MRI) is a non-invasive imaging technique which has become widely used in medicine due to its ability to produce high quality images without the use of ionising radiation. Conventional clinical MRI relies on the fact that hydrogen nuclei ($^{1}H$) present in the body (eg as water molecules) absorb and re-emit energy at a characteristic radio frequency when placed in a strong magnetic field. It is possible to detect the abundance of hydrogen nuclei present in the body, their location, and the type of tissue in which they are present using various well known MRI techniques. Contrast agents such as gadolinium are available which alter the appearance of a tissue in which they are present, making that tissue more visible to $^{1}H$ MRI. Other nuclei such as, for example, sodium ($^{23}Na$), fluorine ($^{19}F$) and carbon ($^{13}C$) yield an MRI signal, though their use is far less developed than the use of hydrogen nuclei.

MRI has also been used in experimental studies of GI transit. Such studies have involved the ingestion by a patient of capsules containing MRI-detectable materials, typically gadolinium-doped water. In other studies, capsules also contained a fluorine-containing compound detectable by $^{19}F$ (as opposed to $^{1}H$) MRI.

Whilst such studies have shown that MRI methods can in principle be used to monitor GI transit, those methods hitherto proposed suffer from a number of disadvantages. The capsules that are used have necessarily been rather large, typically with dimensions of 20 mm or more. This makes them relatively difficult to ingest, particularly for elderly or paediatric patients. More significantly, such large capsules may not pass through the GI tract in a manner that is truly representative of GI transit. In particular, the capsules may leave the stomach rather more slowly than food, but then pass through the rest of the GI tract more quickly. In the case of methods involving more than one MRI nuclide (ie more than one MRI-dectable nucleus, eg $^{1}H$ and $^{19}F$), the methods may be difficult or impossible to carry out using standard MRI scanners, which are normally designed only for $^{1}H$ MRI.

Disorders of the GI tract are a particular problem amongst paediatric patients. Nine percent of children worldwide suffer from constipation at some point in their lives. Constipation becomes chronic in a third of these children with a great impact both on their and their families' well-being. Many are referred to hospital and some undergo surgery. In the hospital setting, paediatric constipation forms 3% of all referrals to paediatric practice and up to 25% to paediatric gastroenterologists. Functional constipation can markedly impair quality of life and results in repeated consultations, treatment attempts and various investigations. A recent U.S. study suggests that there is a great cost of health resources for children with constipation, estimated at $3.9 billion/year. In Britain, 34% of children aged 4-11 years are reported to have had constipation. Of these, 5% had complaints for more than 6 months. Managing these young patients is difficult. Direct and early assessment of GI transit time can confirm the presence of slow transit, provide insight into the causes of disease, stratify the patients (e.g. slow-transit constipation and Irritable Bowel Syndrome-constipation), direct therapy and monitor responses. However, at present, this is not done routinely in children because of a lack of standardized methodology and concerns regarding the use of ionising radiation in this young population. In the UK, early use of X-ray and current transit studies are explicitly ruled out by NICE (National Institute for Health and Care Excellence) clinical guidelines and are only to be considered as a specialist service in cases of intractable constipation. Physicians therefore rely mostly on symptoms, often as reported by the child's parents. Uncertainty leads to repeated appointments and treatments, unhappiness with the results and waste of health service resources. Similar concerns apply to other groups for which the use of ionising radiation is precluded, eg pregnant women or women of child-bearing age.

There is thus a need for improved non-invasive methods of monitoring GI transit that accurately reflect the manner in which food is transported through the subject's GI tract. It is particularly desirable that such methods should be applicable to elderly and paediatric patients, and that the methods can be carried out using standard and widely-available equipment.

According to a first aspect of the present invention, there is provided a method of imaging a human or animal subject, which subject has previously ingested a container containing first and second fluids that are detectable and distinguishable by MRI, which method comprises the steps of
   a) forming a first magnetic resonance image of at least a portion of the subject's GI tract in which the container is located, wherein the magnetizations of the first and second fluids are in-phase;
   b) forming a second magnetic resonance image, coincident with the first image, wherein the magnetizations of the first and second fluids are out-of-phase; and
   c) subtracting the second image from the first image, or vice versa, to form a composite image.

The method of the first aspect of the invention is useful as a means of assessing GI transit in the subject. Thus, the invention further provides a method of assessing GI transit in a human or animal subject, which subject has previously ingested a container containing first and second fluids that are detectable and distinguishable by MRI, which method comprises the steps of
   a) at a known time after ingestion of the container by the subject, forming a first magnetic resonance image of at least a portion of the subject's GI tract in which the container is located, wherein the magnetizations of the first and second fluids are in-phase;
   b) forming a second magnetic resonance image, coincident with the first image, wherein the magnetizations of the first and second fluids are out-of-phase;
   c) subtracting the second image from the first image, or vice versa, to form a composite image; and
   d) analysing the composite image to determine the location of the container within the subject's GI tract.

The in-phase and out-of-phase images may be formed directly, eg by double-echo imaging. Alternatively, the images may be formed indirectly, eg using double-echo or multi-echo imaging whereby the magnetizations of the first and second fluids are not imaged in-phase and out-of-phase but in-phase and out-of-phase images are generated by subsequent data processing.

Most commonly, steps a)-d) above will be repeated several times in order to track the progress of the container through the subject's GI tract. Thus, the method may be repeated at intervals over a period of time sufficient to monitor the progress of the container through the GI tract or a part thereof, and to enable a meaningful conclusion to be drawn in relation to the function of the GI tract, or of selected segments of the GI tract, in terms of transit time. Thus, images may be generated a number of times over the course of a time period that is long enough for the passage of the container through the subject's GI tract to be tracked sufficiently for the required clinical assessment of GI function to be possible. Such a time period may be up to 12 hours, or up to 24 hours, or up to 48 hours, or more. The number of times that images are generated during that period may be from 2 to 4, or up to 6, 8, 10, 12 or more.

In general, the method will involve the ingestion of a plurality of containers, not least in order to maximise the likelihood of at least one container being discernible in the MRI images. The number of containers that are ingested will depend on a number of factors, including the size of the containers. As described below, in some embodiments of the invention, the containers have dimensions of the order of a few millimetres. In such cases, the subject may typically ingest up to 24 containers or more, eg from 2 to 20, or from 2 to 10, or from 2 to 8, or from 2 to 6 containers. In other embodiments, also described below, the containers have the form of microparticulates, in which case the number of individual containers may be very large indeed.

Containers may be ingested by the subject at more than one time. Thus, a first container (or a first plurality of containers) may be ingested at a first time, and a second container (or a second plurality of containers) may be ingested at a second, later time. Where containers are ingested at two or more time points, it may be desirable to distinguish those containers from each other. This may be achieved by various means. For instance, the containers may have different shapes that are discernible in the MRI images. Alternatively, one or both of the fluids in the different containers may be distinguishable on the basis of their MRI properties. For instance, one of the fluids may be water doped with differing concentrations of a contrast agent such as gadolinium, the effect of which is that the aqueous fluids in different containers have differing relaxation times, so that they can be distinguished from each other by appropriate choice of imaging parameters.

"Detectable by MRI" when applied to the first and second fluids in the context of the first aspect of the present invention means simply that the fluid contains nuclei that absorb and re-emit radiofrequency electromagnetic radiation in a manner that allows the generation of an image using standard MRI techniques. Typically, the fluid contains $^1H$ nuclei, so that images may be generated using MRI equipment adapted, as most such equipment is, for the imaging of $^1H$-containing material. The first and second fluids necessarily contain the same nuclide, most commonly $^1H$.

"Distinguishable by MRI" when applied to the first and second fluids in the context of the first aspect of the present invention means that the nuclide of interest (most commonly $^1H$ nuclei) has somewhat different nuclear magnetic resonance properties in one fluid than in the other. In general, this means that, at any given magnetic field strength, the nuclide of one of the fluids has a slightly different resonant frequency to the resonant frequency of the same nuclide in the other fluid. This is commonly referred to as one of the fluids having a slightly different chemical shift to that of the other fluid.

The first and second fluids are thus conveniently fluids that contain an abundance of the same nuclide, but in which that nuclide occupies different chemical environments such that the resonant frequencies of the nuclide in the two fluids differ sufficiently. Preferably, the fluids are also such that they are non-toxic and physiologically compatible, so that they do not present a risk to the subject if released from the container. A particularly convenient combination of first and second fluids is water (or a water-containing aqueous medium) and an oil.

Typically, the first fluid is aqueous. Thus, the first fluid may be water or an aqueous solution, or as described below it may be the aqueous phase of an oil-in-water or water-in-oil emulsion. The first fluid may contain a solute that modifies the MRI properties of the first fluid. Such a solute may be a material that is known for use as a contrast agent in MRI. Such materials typically function by altering the magnetic resonance relaxation times of the first fluid, and include gadolinium salts and other paramagnetic ions. The nature of the first and second images, and hence of the composite image, may be optimised by appropriate choice of the concentration of the solute in the first fluid.

A wide variety of oils may be suitable for use as the second fluid. Typically, such oils include oils from vegetable, marine or animal sources. For instance, the oil may be selected from the group consisting of well known and widely available oils such as olive oil, corn oil, soybean oil, canola oil, cottonseed oil, coconut oil, sesame oil, sunflower oil, borage seed oil, hempseed oil, herring oil, cod-liver oil, salmon oil, flaxseed oil, wheat germ oil, evening primrose oil, and mixtures thereof.

Other forms of oil, such as mineral oils and silicone oils may also be suitable. However, the use of an oil that is found in foodstuffs, and hence is known to be non-toxic in the event that it were to be released from the container within the subject's GI tract, is preferred.

The first fluid and/or second fluid may have the form of a gel. The gel may be one that is relatively solid at ambient temperature, to facilitate manufacture, handling and administration to the subject, but which becomes fluid, and therefore easier to image by MRI, at body temperature.

The method of the first aspect of the invention requires the generation of two images: a first image in which the magnetizations of the first and second images are in-phase and a second image in which the magnetizations are out-of-phase. The meanings of these terms, and ways in which such images may be generated, will be familiar to those skilled in the art of MRI. However, briefly described with reference to $^1$H nuclides in oil and water, when the container containing the two fluids is positioned within a magnetic field, the net magnetization of the $^1$H nuclides of each fluid can be represented as a vector that precesses around the axis of the applied magnetic field. However, the precession frequency of the $^1$H nuclides in the first fluid (oil) will be slightly different to that of the $^1$H nuclides in the second fluid (water), ie the two fluids have different chemical shifts. The magnetizations of the two fluids will therefore precess at different rates, and as they do so they also lose coherence. The generation of an image normally involves the application of a series of radiofrequency pulses, the effect of which is to restore the coherence of the precessing magnetizations. By appropriate choice of time interval between radiofrequency pulses, images may be generated with the magnetization vectors of the nuclides in the first and second fluids in alignment (in-phase) or with the magnetizations opposed (out-of-phase). As noted above, it is also possible to generate double-echo and also multiple-echo images which are not exactly in-phase and out-of-phase but can be post-processed to reconstruct mathematically an in-phase and an out-of-phase pair of images.

The second image is coincident with the first image. By this meant that the second image matches the first image both spatially and temporally. By "temporally coincident" is meant that the time interval between generation of the first and second images is sufficiently short that any displacement of any features of the image during that interval are negligible. In particular, the interval between generation of the first image and the second image should be such that no significant displacement of the container occurs during that interval. In practice, however, this interval is usually only a few milliseconds and so displacement is unlikely.

If there is some spatial displacement of the second image relative to the first image (eg in the event that the subject moves slightly between generation of the first and second images), then an appropriate correction may be applied to one or both images to realign them, as part of the data processing prior to subtraction of one image from the other.

The final step of the method according to the first aspect of the invention involves processing of the first and second images by subtracting one from the other in order to create a composite image. Data processing of this kind is standard practice in MRI, and the methods and equipment necessary to bring it about will be familiar to those skilled in the art. In general, each image consists of an array of pixels (picture elements) or voxels (volume elements), the values of which represent the intensities of the MRI image at those locations. Subtraction of one image from the other essentially involves subtracting the value of each pixel/voxel in one image from that of the corresponding pixel/voxel in the other. An important result of this process is that pixels or voxels of background features of the images containing mostly water but not much fat (like muscles) or mostly fat but not much water (like visceral fat), will have similar intensity in both the first and second images: they will be therefore markedly diminished in intensity in the composite subtraction image. On the other hand, pixels or voxels of features of the images containing a mixture of fat and water (like the capsules) will have high intensity on one image and low intensity in the other: they will therefore remain bright in the composite (subtraction) image. The contrast of the image is thereby increased, leading to greater ease and precision in the identification of the positions of the container within the subject's GI tract. The enhancement of the image may facilitate automated or semi-automated identification of the position of the container within the GI tract.

The methods of the present invention may utilise the magnetic resonance properties of any nuclide. However, in the overwhelming majority of cases the nuclide of interest will be $^1$H. Standard, commercially available MRI equipment is adapted for $^1$H imaging, and suitable fluids for use in the invention contain high proportions of $^1$H nuclei (eg water and vegetable oils and the like).

The methods by which the MRI images are generated may involve any suitable MRI techniques. These include, without limitation, selective/suppressed imaging, T1-weighted imaging, T2-weighted imaging, Chemical Exchange Saturation Transfer (CEST) imaging, and diamagnetic CEST (DIACEST) imaging.

The container preferably has the form of a capsule or the like, ie a hollow shell, bead or coated bead/droplet, within which the first and second fluids are contained. The wall of the container should be such that it retains its integrity in the acid environment of the stomach and the alkaline conditions prevalent in the intestines.

The container may comprise separate compartments for the first and second fluids. However, it is particularly preferred that the first and second fluids occupy precisely the same spatial locations. Thus, the first and second fluids may be intimately mixed. Hence, the first and second fluids may constitute distinct phases of a colloidal dispersion such as an emulsion. The emulsion may be an oil-in-water emulsion or a water-in-oil emulsion.

The container preferably has sufficiently small dimensions that it may easily be ingested by the subject, even if the subject is an elderly person or a child. Preferably, the dimensions of the container do not exceed 10 mm. More preferably, the dimensions of the container do not exceed 5 mm. The dimensions of the container may be of the order of 1 mm or 2 mm or 3 mm. Thus, the container may have a maximum dimension of from 0.5 mm to 10 mm, or from 0.5 mm to 5 mm, or from 0.5 mm to 3 mm.

The container may be spherical or non-spherical, eg oval or oblong. Spherical containers may be preferred for reasons of manufacturing simplicity, particularly in the case of very small containers. However, non-spherical containers may be more readily discernible in MRI images and oblong containers may be easier to swallow than disk or spherical shapes In other embodiments, the containers are smaller, and have the form of hollow particles filled with MRI-detectable fluid. Such particles are typically, though not necessarily, generally spherical or oblong, with diameters or other dimensions of the order of 2 mm or less, eg between 0.01 mm and 1 mm. The particles may be administered as a suspension or slurry that may be relatively easy for the subject to ingest. For instance, the particles may be suspended in a liquid or viscous medium to form a drink.

Suitable microparticulate containers may resemble commercially available microcapsules such as those available from Ashland (www.ashland.com) under the trade name ISP MicroCapsules, but formed from, or coated with, a material that maintains its integrity during passage through the GI tract.

Such small particulates may comprise both the first and second fluids, especially where the first and second fluids are intimately mixed, as in an emulsion. Alternatively, the particulates may contain just one of the fluids, but may be administered as a mixture of particulates containing the first fluid and particulates containing the second fluid.

Small fluid-filled particulates of this kind will generally not be individually discernible in MRI images, but will collectively be apparent as a diffuse cloud of material, the progress of which through the GI tract can be followed by the method of the invention.

Whatever the nature of the containers, they preferably have a density that is comparable with that of the stomach contents, ie ingested food material and chyme, so that the containers do not sink to the base of the stomach or float within the stomach, which could delay the passage of the container from the stomach. Thus, the container preferably has a density of 1.0-1.5 $g/cm^3$, more preferably 1.0-1.2 $g/cm^3$.

The use of capsules containing oil in the monitoring of GI transit by MRI is believed to be novel, and represents a further aspect of the invention. According to that aspect of the invention, there is provided a method of imaging a human or animal subject, which subject has previously ingested a container containing an oil that is detectable by MRI, which method comprises forming a magnetic resonance image of at least a portion of the subject's GI tract in which the container is located.

Whereas endogenous water present within the GI tract and the surrounding tissues may make it difficult to discern water-based markers in the methods of the invention, it has been found that this is not such a problem for oil-based markers. It is believed that this because the lumen of the GI tract would in general not be expected to contain pockets of substantial quantities of material having similar MRI properties to the oils that are useful in the present invention (eg fat and the like).

A related aspect of the invention is a method of assessing GI transit in a human or animal subject, which subject has previously ingested a container containing an oil that is detectable by MRI, which method comprises the steps of
 a) at a known time after ingestion by the subject of the container, forming a magnetic resonance image of at least a portion of the subject's GI tract in which the container is located; and
 b) identifying the location of the container within the subject's GI tract at said time.

Another aspect of the invention that is believed to be novel is the use of a plurality of markers that are detectable and distinguishable by MRI, and which are ingested at different times, in a method of assessing GI transit. Thus, according to another aspect of the invention, there is provided a method of assessing GI transit in a human or animal subject, which method comprises the steps of
 a) at a time point after the subject has ingested a first form of MRI-detectable and MRI-distinguishable marker, forming a magnetic resonance image of at least a portion of the subject's GI tract in which the first form of marker is located; and
 b) at a time point after the subject has ingested a second form of MRI-detectable and MRI-distinguishable marker, forming a magnetic resonance image of at least a portion of the subject's GI tract in which the second form of marker is located.

This aspect of the invention may of course involve further forms of marker, eg third and fourth forms of marker. As described above in relation to the first aspect of the invention, the different forms of marker may be distinguishable by various means. For instance, the containers may have different shapes that are discernible in the MRI images. Alternatively, the markers may be distinguishable on the basis of their MRI properties. For instance, the markers may be containers filled with materials having differing MRI properties, eg water doped with differing concentrations of a contrast agent such as gadolinium, the effect of which is that the aqueous fluids in different containers have differing relaxation times, so that they can be distinguished from each other by appropriate choice of imaging parameters.

The methods of the invention are particularly useful in the assessment of GI transit in paediatric patients, young patients (eg up to 21 years of age) and women of child-bearing age. In such patients, conventional use of X-Rays is discouraged. MRI markers that are small are relatively easy to ingest and behave within the GI tract in a manner that is representative of GI transit in the subject. Thus, the invention further provides a method of assessing GI transit in a human or animal subject, which subject has previously ingested a plurality of MRI-detectable markers having maximum dimensions of less than 5 mm, which method comprises forming a magnetic resonance image of at least a portion of the subject's GI tract in which the markers are located.

The MRI markers employed in this aspect of the invention may be any of those described above, ie containers holding first and second fluids (eg oil and water or an emulsion), containers of oil, or containers of water, or containers of a solution of an MRI contrast agent. The number and nature of the containers, the number of times that images are generated and the timescale over which images are generated may be as described above.

The methods of the invention involve the use of novel MRI-detectable markers. According to a further aspect of the invention, there is therefore provided a kit comprising a plurality of MRI-detectable markers suitable for use in any of the foregoing methods, together with instructions for their use in any one of those methods.

As described above, the markers may take the form of containers holding first and second fluids (eg oil and water or an emulsion), containers of oil, or containers of water, or containers of a solution of an MRI contrast agent.

Markers useful in the methods of the invention are also believed to be novel, and represent a further aspect of the invention, which thus provides a marker for use in MRI of a human or animal subject, the marker comprising a container containing first and second fluids that are detectable and distinguishable by MRI.

As described above, the first and second fluids may be water (or a water-containing aqueous medium) and an oil, and in certain embodiments, the first and second fluids together form an emulsion.

In another aspect of the invention, there is provided a marker for use in MRI of a human or animal subject, the marker comprising a slurry or suspension of hollow particles containing an MRI-detectable fluid. In some embodiments, the fluid may comprise an oil. In some embodiments, the fluid may comprise an oil-in-water emulsion or a water-in-oil emulsion.

The instructions may comprise instructions to calculate a geometric centre score (as described below) and may comprise information regarding example geometric centre scores. The instructions may comprise an indication of one or more normal geometric centre scores and/or one or more abnormal geometric centre scores.

The instructions may comprise a chart illustrating the notional sections of the body structure.

The methods of the invention are all useful in the assessment of GI transit. The methods may be used to study whole gut transit or transit through a region of the GI tract, eg small bowel transit, colonic transit or regional colonic transit.

The assessment of GI transit may comprise noting an administration time at which the or each marker is administered to the subject, determining the location for the or each marker within the GI tract of the subject by a method described above, and using the location(s), together with the time that has elapsed between administration and imaging, to produce a score indicative of the transit of the marker(s).

The assessment of GI transit may comprise determining an average transit time. Assessing the transit may comprise simply summing how many capsules are present in any given segment of the GI tract at a given time point and using simple calculations to assign a transit time, or determining a geometric centre score indicative of the transit time. Determining the geometric centre score may comprise the step of notionally dividing the GI tract into a plurality of notional sections. The method may comprise noting how many markers are found in each of the notional sections at the (or each) imaging time.

Each notional section may be assigned a number. The method may comprise multiplying the number of markers found in a respective section (if any) by the number assigned to that section to produce a weighted number of markers for that section. The method may comprise summing the weighted numbers for each section (or each non-zero weighted number) and dividing by the total number of markers ingested to produce a geometric centre score.

Specific embodiments of the invention include the following.

a) A method of assessing GI transit in a human or animal subject, which method involves ingestion by the subject of a container (or more usually a plurality of containers) containing two different fluids that can be detected and distinguished by MRI. The two fluids may be water (or more commonly an aqueous solution) and an oil, and may be in the form of an emulsion. The containers may be capsules or the like, beads, or coated drops/beads, with sizes of the order of a few millimetres, or they may be microcapsules of much smaller size. In the latter case, the containers may be ingested in the form of a suspension or slurry. At a series of time points subsequent to ingestion of the container(s), images are generated of the subject's GI tract, so that the progess of the container(s) can be monitored. The identification of the location of the container(s) at each measured time point is facilitated by the generation of a composite image, as described above. A defined assessment scheme may be used to evaluate the results, enabling the required clinical assessment of GI function to be made.

b) A method of assessing GI transit in a human or animal subject, which method involves ingestion by the subject of a container (or more usually a plurality of containers) containing an oil that is detectable by MRI. The containers may be capsules or the like, with sizes of the order of a few millimetres, or they may be microcapsules of much smaller size. In the latter case, the containers may be ingested in the form of a suspension or slurry. At a series of time points subsequent to ingestion of the container(s), images are generated of the subject's GI tract, so that the progress of the container(s) can be monitored. A defined assessment scheme may be used to evaluate the results, enabling the required clinical assessment of GI function to be made.

c) A method of assessing GI transit in a child, which method involves ingestion by the child of a plurality of small MRI-detectable markers (with dimensions of less than 5 mm). The containers may be capsules or the like, or they may be microcapsules of much smaller size. In the latter case, the containers may be ingested in the form of a suspension or slurry. The containers may contain an oil that is detectable by MRI. The containers may contain two different fluids that can be detected and distinguished by MRI. The two fluids may be water (or more commonly an aqueous solution) and an oil, and may be in the form of an emulsion. At a series of time points subsequent to ingestion of the container(s), images are generated of the subject's GI tract, so that the progess of the container(s) can be monitored. A defined assessment scheme may be used to evaluate the results, enabling the required clinical assessment of GI function to be made.

The principle underpinning the methods of the invention will now be illustrated with reference to the accompanying FIG. 1, which shows $^1$H MRI images of a test rig comprising a pair of vials containing agar gel within which sunflower seeds are dispersed. Sunflower seeds are suitable models for illustration of the present invention since they contain moisture and oil, the oil being present in micropockets within the seeds. In addition, the test rig contains a water phantom (i.e. a water-filled feature)—the circular feature at the right of each image—and an oil phantom—the generally semicircular feature to the left of each image.

The images are the following:
a) This image is generated under MRI conditions that reveal only the water-containing component of the test rig. The vials are visible, as are the sunflower seeds (as regions of reduced intensity) within the vials. The water phantom is clearly visible, but not the oil phantom.
b) This image was generated under MRI conditions that reveal only the oil-containing component of the test rig. Thus only the oil phantom and the sunflower seeds are clearly visible, the latter as bright spots. This illustrates the feasibility of the use of oil-containing capsules or particles in the methods of the invention.
c) This image was calculated to show the magnetizations of the oil and water in-phase. This image thus corresponds to the "first image" of the first aspect of the invention. The water and oil phantoms are clearly visible, as are the vials, but the contrast between the sunflower seeds and the surrounding agar gel is rather low.
d) In this image, the magnetizations of the oil and water are shown out-of-phase. The image thus constitutes the "second image". Again, both oil and water phantoms are visible, and the sunflower seeds are readily visible (as areas of reduced intensity compared with that of the surrounding agar gel).
e) Finally, this composite image was obtained by subtraction of image c) from image b). The sunflower seeds are readily visible as bright spots against a uniform grey background.

The invention claimed is:

1. A method of imaging a human or animal subject that has ingested a container containing first and second fluids that are detectable and distinguishable by MRI comprising:

forming a first magnetic resonance image of at least a portion of the subject's GI tract in which the container is located, wherein the first and second fluids contain $^1H$ and the magnetizations of the first and second fluids are in-phase;

forming a second magnetic resonance image, coincident with the first image, wherein the magnetizations of the first and second fluids are out-of-phase;

subtracting the second image from the first image, or the first image from the second image, to form a composite image; and analysing the composite image to determine a location of the container within the subject's GI tract.

2. The method of claim 1, wherein the subject has ingested a plurality of containers.

3. The method of claim 1, wherein containers are ingested by the subject at two or more time points and are distinguishable from each other.

4. The method of claim 3, wherein the containers are distinguishable by virtue of having different shapes that are discernible in the MRI images.

5. The method of claim 3, wherein the containers are distinguishable on the basis of their MRI properties.

6. The method of claim 1, wherein the first and second fluids are water, or a water-containing aqueous medium; and an oil.

7. The method of claim 1, wherein the container has the form of a capsule having a hollow shell within which the first and second fluids are contained, and the wall of the container is such that it retains its integrity in the acid environment of the stomach and the alkaline conditions prevalent in the intestines.

8. The method of claim 7, wherein the container comprises separate compartments for the first and second fluids.

9. The method of claim 7, wherein the first and second fluids constitute distinct phases of a colloidal dispersion such as an emulsion.

10. The method of claim 1, wherein the container has a maximum dimension of from 0.5 mm to 10 mm.

11. The method of claim 1, wherein the container is a hollow particle filled with MRI-detectable fluid.

12. The method of claim 11, wherein the particle is generally spherical or oblong, with diameters or other dimensions of the order of 2 mm or less.

13. The method of claim 12, wherein particles are administered as a suspension or slurry.

14. The method of claim 1, wherein the forming the first magnetic resonance image, forming the second magnetic resonance image, subtracting the second image from the first image, or the first image from the second image, to form a composite image, and analysing the composite image steps are repeated several times in order to track the location of the container through the subject's GI tract over a period of time.

* * * * *